United States Patent
Shazly et al.

(10) Patent No.: US 8,574,224 B2
(45) Date of Patent: Nov. 5, 2013

(54) SURGICAL LASER DEVICE UTILIZING A VISIBLE LASER DIODE

(76) Inventors: Tarek A. Shazly, Reading, MA (US); Mark A. Latina, North Andover, MA (US)

( * ) Notice: Subject to any disclaimer, the term of this patent is extended or adjusted under 35 U.S.C. 154(b) by 393 days.

(21) Appl. No.: 12/906,372

(22) Filed: Oct. 18, 2010

(65) Prior Publication Data
US 2011/0098692 A1    Apr. 28, 2011

Related U.S. Application Data

(60) Provisional application No. 61/364,584, filed on Jul. 15, 2010, provisional application No. 61/254,360, filed on Oct. 23, 2009.

(51) Int. Cl.
*A61B 18/20*    (2006.01)

(52) U.S. Cl.
USPC ................................... 606/10; 606/3; 606/17

(58) Field of Classification Search
USPC ............... 606/3–6, 8–14, 16–18; 607/88–92; 128/898
See application file for complete search history.

(56) References Cited

U.S. PATENT DOCUMENTS

| | | | |
|---|---|---|---|
| 4,580,557 A * | 4/1986 | Hertzmann | 606/12 |
| 6,530,918 B1 * | 3/2003 | Ueno et al. | 606/10 |
| 2004/0116909 A1 | 6/2004 | Neuberger et al. | |
| 2005/0143720 A1 | 6/2005 | Yamada et al. | |
| 2005/0203593 A1 | 9/2005 | Shanks et al. | |
| 2005/0240168 A1 | 10/2005 | Neuberger et al. | |
| 2008/0015553 A1 * | 1/2008 | Zacharias | 606/4 |
| 2008/0108983 A1 * | 5/2008 | Nadolski | 606/16 |
| 2008/0269847 A1 | 10/2008 | Nemenov | |
| 2010/0318074 A1 * | 12/2010 | Dacquay et al. | 606/4 |

OTHER PUBLICATIONS

International Search Report for International Application No. PCT/US10/053013, dated Dec. 6, 2010.

* cited by examiner

*Primary Examiner* — Ahmed Farah
(74) *Attorney, Agent, or Firm* — Morse, Barnes-Brown & Pendleton, P.C.; Sean D. Detweiler, Esq.

(57) ABSTRACT

Systems, apparatuses, and methods for a compact surgical device include a laser unit and one or more laser outlet assemblies. The laser unit has a power regulator, one or more diode laser assemblies, each having a single diode laser source, and a laser trigger mechanism. The laser unit can emit an aiming light beam and a treatment laser beam either both from the same single diode laser or from two separate single diode lasers. The beam can pass through the one or more laser outlet assemblies. The aiming light beam can have a first energy level. The treatment laser beam can have a second energy level that is substantially greater than the first energy level of the aiming light beam.

30 Claims, 8 Drawing Sheets

SURGICAL LASER DEVICE UTILIZING A VISIBLE LASER DIODE

RELATED APPLICATIONS

This application claims priority to, and the benefit of, co-pending U.S. Provisional Application 61/364,584, filed Jul. 15, 2010, for all subject matter common to both applications. This application also claims priority to, and the benefit of, co-pending U.S. Provisional Application 61/254,360, filed Oct. 23, 2009, for all subject matter common to both applications. The disclosures of said provisional applications are hereby incorporated by reference in their entirety.

FIELD OF THE INVENTION

The present invention relates to systems and methods for providing surgical laser treatments, particularly to a compact visible laser diode device capable of performing desired treatments, including but not limited to, photocoagulation.

BACKGROUND OF THE INVENTION

In the current state of the art of photocoagulative laser surgery, a treatment laser beam and an aiming light beam originate from two different sources, requiring a series of optical elements employed for superposing both laser beams with a very high degree of precision. The common path for the aiming and treatment beam usually involves a fiber optic cable that is both high maintenance and expensive. More control and directing means are required to modify the beam at the entrance of an operating optical system essentially formed, e.g., by a slit lamp. Other types of laser devices can likewise demonstrate similar characteristics and complexities. These complexities of conventional laser system designs can significantly add to the cost, size, and weight of the systems, and increase the chances of machine failure.

SUMMARY

There is a need in the art for a laser device providing a more simplified control and directing means. Additionally, there is a need for a laser device that does not require complex superposing methods and equipment for aligning an aiming light beam with a laser treatment beam. The present invention is directed toward further solutions of these needs, in addition to having other beneficial properties.

According to one embodiment of the present invention, a compact surgical apparatus has a laser unit. The laser unit has a power regulator, a diode laser assembly having a single diode laser source, a laser trigger mechanism. The compact surgical apparatus also has a laser outlet assembly. The laser unit can emit an aiming light beam and a treatment laser beam both from the single diode laser through the laser outlet assembly. The aiming light beam can have a first energy level and the treatment laser beam can have a second energy level that is substantially greater than the first energy level of the aiming light beam.

According to aspects of the present invention, the laser unit can emit energy in a wavelength within the visible spectrum. The laser unit can also emit energy at a wavelength of about 405±20 nm, about 445±20 nm, about 635±20 nm, about 658±20 nm, and/or about 520±20 nm. The laser unit can have a lasing threshold. The first energy level can be below the lasing threshold, and the second energy level can be above the lasing threshold. The power regulator can be configured to supply the diode laser assembly with a current of about 10-100 mA or about 500-2,000 mA. The aiming light beam and the treatment laser beam can each have a spot size of about 50 microns. The laser unit can also include a timer circuit for activating one or more predetermined, adjustable pulses. The laser outlet assembly can include a lens assembly including one or more lenses configured to direct the paths of the aiming light beam and the treatment laser beam.

According to another embodiment of the present invention, a system for surgical procedures includes a compact surgical apparatus. The compact surgical apparatus includes a laser unit. The laser unit can include a power regulator, a diode laser assembly having a single diode laser source, and a laser trigger mechanism. The compact surgical apparatus also has a laser outlet assembly. The laser unit can emit an aiming light beam and a treatment laser beam both from the single diode laser through the laser outlet assembly. The aiming light beam can have a first energy level and the treatment laser beam can have a second energy level that is substantially greater than the first energy level of the aiming light beam. The system can further include an operating optical system coupled with the compact surgical apparatus.

According to further aspects of the present invention, the laser unit can emit energy in a wavelength within the visible spectrum. The laser unit can emit energy at a wavelength of about 405±20 nm, about 445±20 nm, about 635±20 nm, about 658±20 nm, and/or about 520±20 nm. The laser unit can have a lasing threshold. The first energy level can be below the lasing threshold and the second energy level can be above the lasing threshold. The power regulator can be configured to supply the diode laser assembly with a current of about 10-100 mA or about 500-2,000 mA. The aiming light beam and the treatment laser beam can each have a spot size of about 50 microns. The system can further include a timer circuit for activating one or more predetermined, adjustable pulses. The laser outlet assembly can include a lens assembly of one or more lenses for directing the paths of the aiming light beam and the treatment laser beam.

According to yet another embodiment of the present invention, a method of using a compact surgical apparatus includes providing power to a diode laser assembly of a laser unit having a single diode laser source through a power regulator. The method can include controlling a power level of the laser unit using the power regulator to emit an aiming light beam from the single diode laser at a first power level. The method can further include activating a trigger to initiate a treatment laser pulse from the single diode laser of the laser unit having a second power level substantially greater in magnitude than the first power level of the aiming light beam. Finally, the method can include emitting the treatment laser pulse to a targeted treatment area.

According to yet further aspects of the present invention, the laser unit can emit energy in a wavelength within the visible spectrum. The laser unit can also emit energy at a wavelength of about 405±20 nm, about 445±20 nm, about 635±20 nm, about 658±20 nm, and/or about 520±20 nm. The laser unit can have a lasing threshold. The first power level can be below the lasing threshold and the second power level can be above the lasing threshold. The aiming light beam and the treatment laser beam can each have a spot size of about 50 microns.

According to further aspects of the present invention, using the power regulator can include using the power regulator to supply the diode laser assembly with a current of about 10-100 mA. Activating a trigger can include activating a trigger to supply a current of about 500-2,000 mA from the power regulator to the laser diode assembly. The method can include directing the paths of the aiming light beam and the treatment laser beam with a lens assembly comprising one or more lenses. Further, the method can include emitting one or more subsequent predetermined, adjustable treatment laser pulses using a timer circuit.

According to yet another embodiment of the present invention, a compact surgical apparatus has a laser unit. The last unit has a power regulator, a first diode laser assembly having a single diode laser source, a second diode laser assembly having a single diode laser source, and a laser trigger mechanism. The compact surgical apparatus can also have a laser outlet assembly. The laser unit can emit an aiming light beam and a treatment laser beam both from of the first diode laser assembly and the second diode laser assembly through the laser outlet assembly. The aiming light beam can have a first energy level and the treatment laser beam can have a second energy level that is substantially greater than the first energy level of the aiming light beam.

According to further aspects of the present invention, the laser unit can emit energy in a wavelength within the visible spectrum. The laser unit can also emit energy at a wavelength of about 405±20 nm, about 445±20 nm, about 635±20 nm, about 658±20 nm, and/or about 520±20 nm. The laser unit can have a lasing threshold. The first energy level can be below the lasing threshold and the second energy level can be above the lasing threshold. The power regulator can be configured to supply the first diode laser assembly with a current of about 10-100 mA and the second diode laser assembly with a current of about 500-2,000 mA. The aiming light beam and the treatment laser beam each can have a spot size of about 50 microns. The compact surgical apparatus can further include a timer circuit for activating one or more predetermined, adjustable pulses. The laser outlet assembly can include a lens assembly of one or more lenses configured in such a way as to direct the paths of the aiming light beam and the treatment laser beam.

According to another embodiment of the present invention, a compact surgical apparatus has a laser unit. The laser unit can have a power regulator, a first diode laser assembly having a single diode laser source, a second diode laser assembly having a single diode laser source, a laser trigger mechanism, a first laser outlet assembly, and a second laser outlet assembly. The laser unit can emit an aiming light beam and a treatment laser beam both from both of the first diode laser assembly and the second diode laser assembly through the first and second laser outlet assembly. The aiming light beam can have a first energy level and the treatment laser beam can have a second energy level that is substantially greater than the first energy level of the aiming light beam.

In accordance with further aspects of the present invention, the laser unit can emit energy in a wavelength within the visible spectrum. The laser unit can also emit energy at a wavelength of about 405±20 nm, about 445±20 nm, about 635±20 nm, about 658±20 nm, and/or about 520±20 nm. The laser unit can have a lasing threshold. The first energy level can be below the lasing threshold and the second energy level can be above the lasing threshold. The power regulator can be configured to supply the first diode laser assembly with a current of about 10-100 mA and the second diode laser assembly with a current of about 500-2,000 mA. The aiming light beam and the treatment laser beam each can have a spot size of about 50 microns. The compact surgical apparatus can include a timer circuit for activating one or more predetermined, adjustable pulses. The compact surgical apparatus further include one or more lens assemblies, each having one or more lenses configured in such a way as to direct the paths of the aiming light beam and the treatment laser beam.

BRIEF DESCRIPTION OF THE DRAWINGS

The present invention will become better understood with reference to the following description and accompanying drawings, wherein.

DETAILED DESCRIPTION

Figure 1:
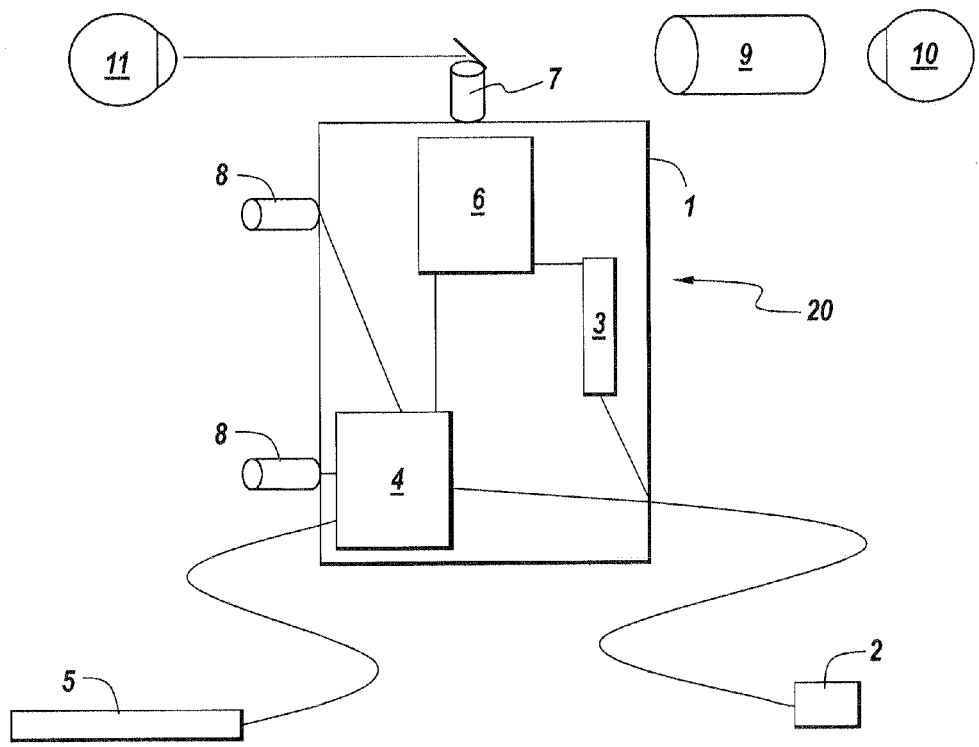
FIG. 1 is a schematic illustration of a compact surgical apparatus according to one embodiment of the present invention.
Figure 2A:
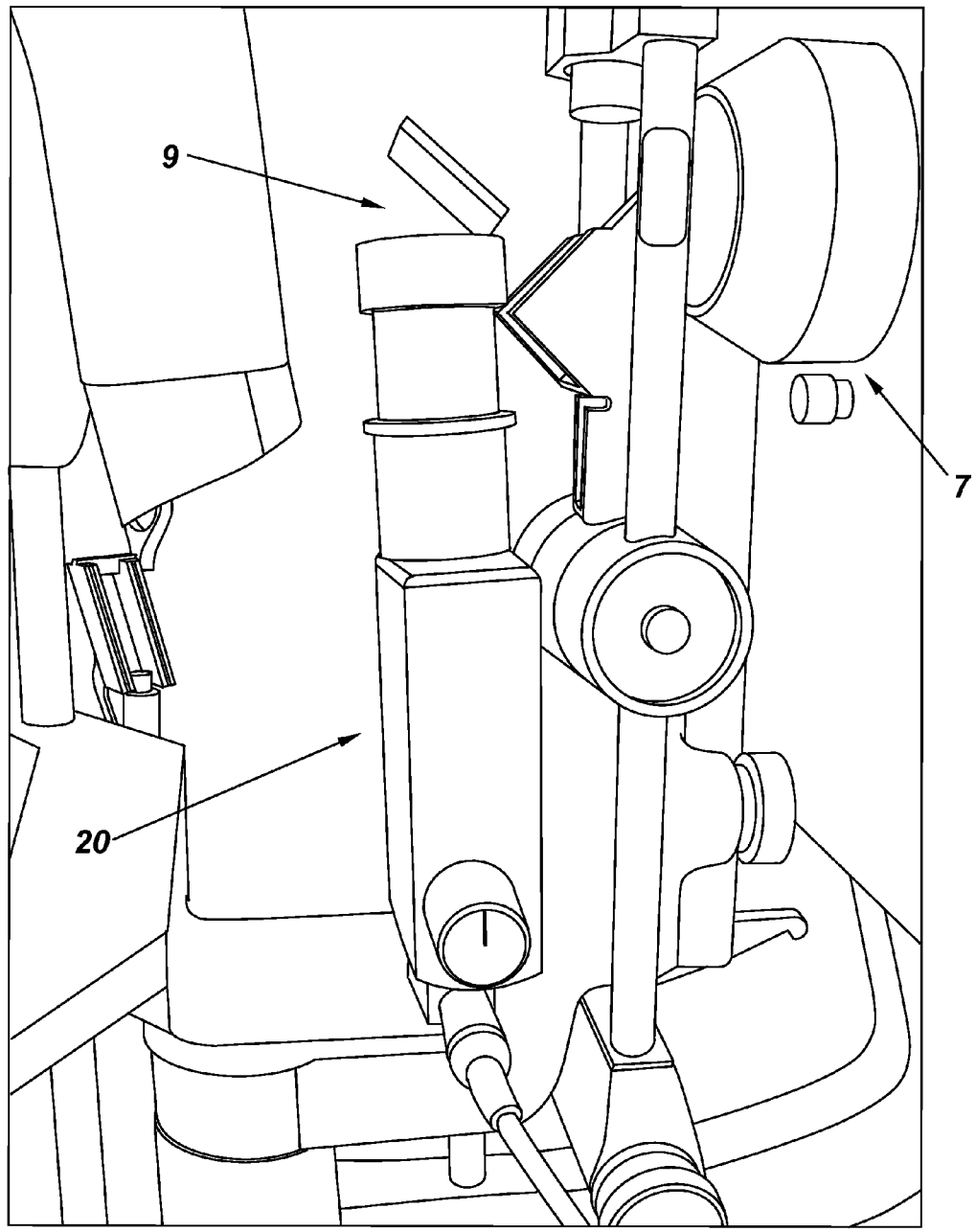
FIG. 2A is a digital photograph of a side view of a prototype compact surgical apparatus according to one embodiment of the present invention.
Figure 2B:
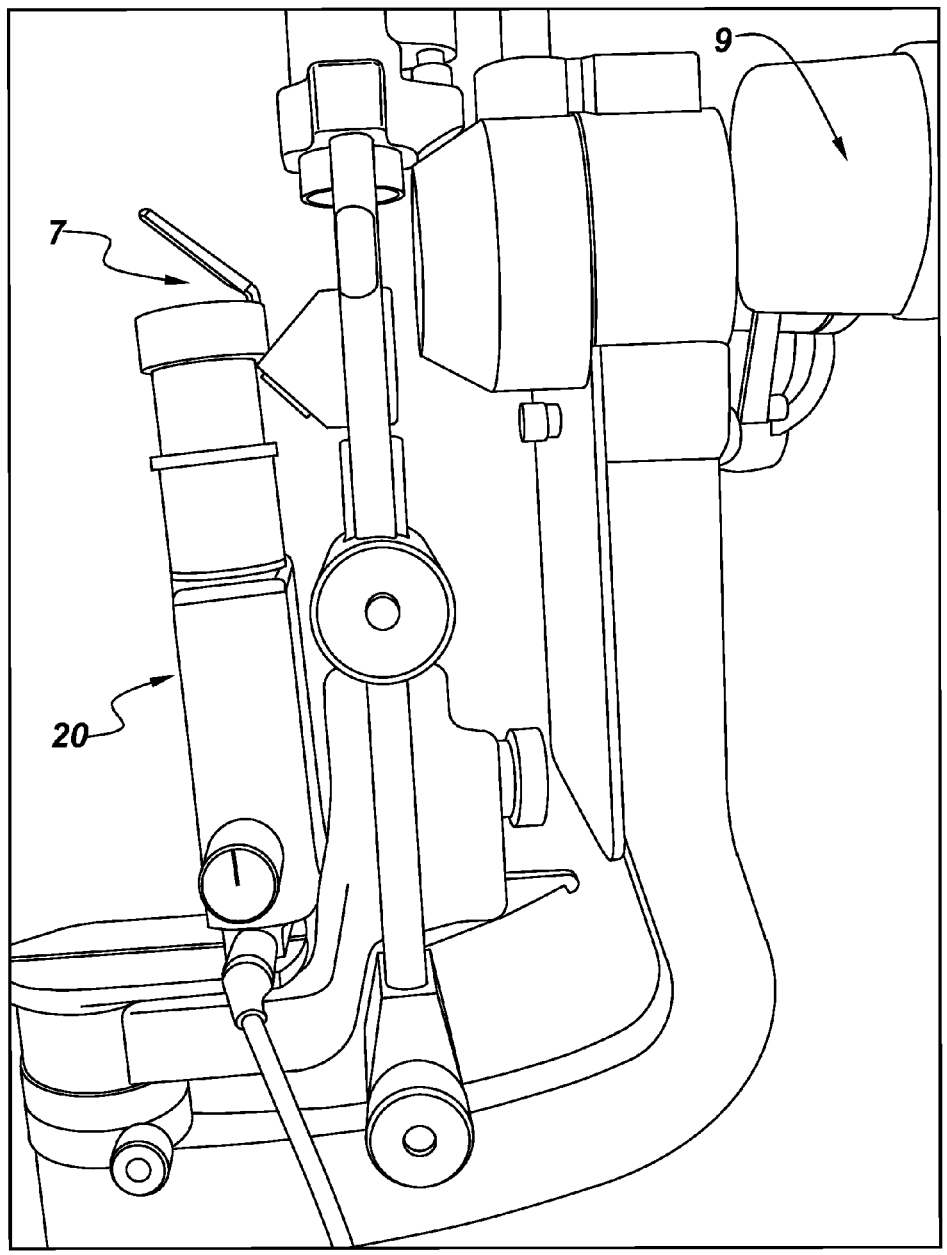
FIG. 2B is a digital photograph of a side view of a prototype compact surgical apparatus according to one embodiment of the present invention.
Figure 3:
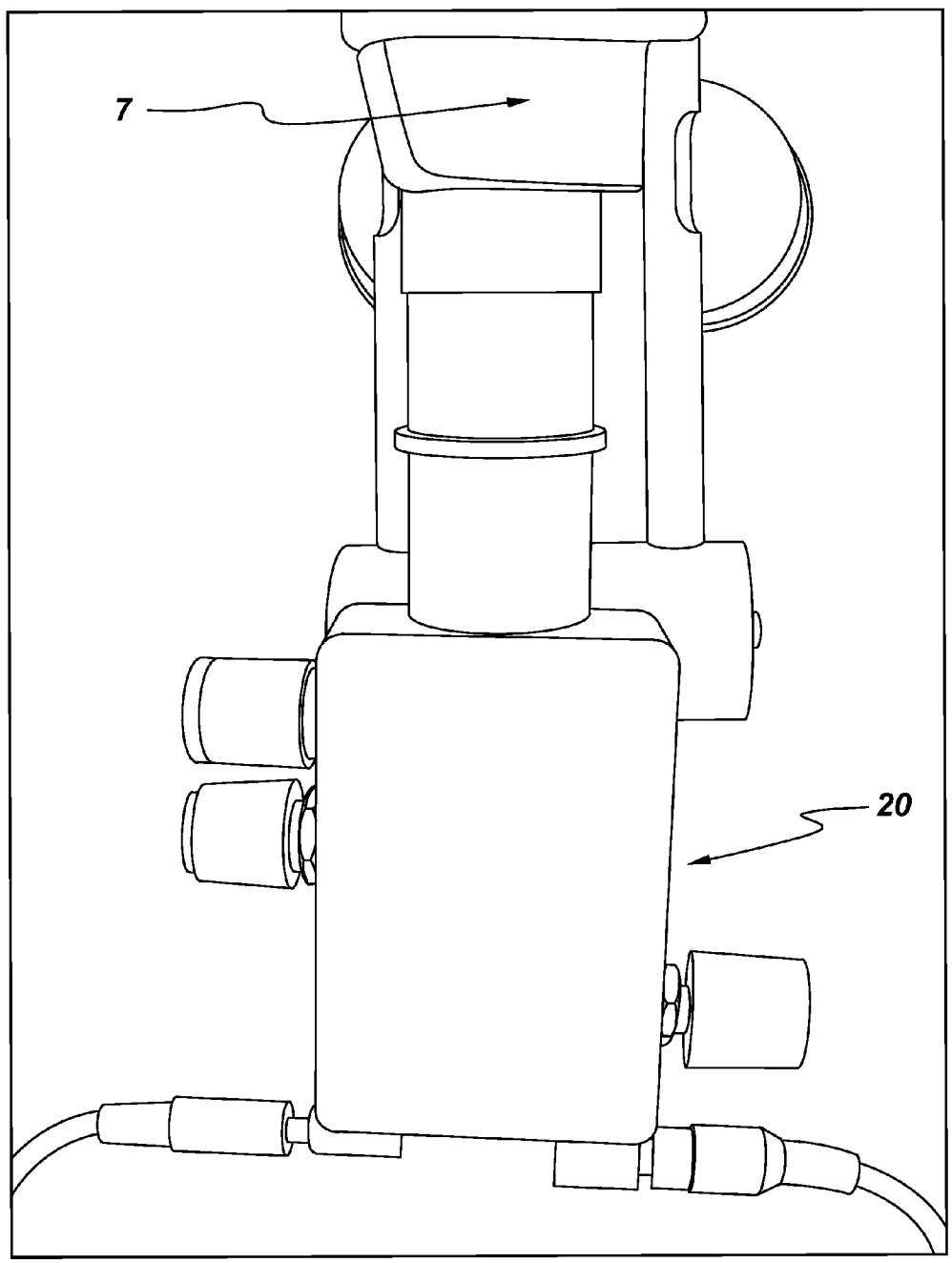
FIG. 3 is a digital photograph of a front view of the apparatus of FIG. 2B, according to one aspect of the present invention.

There is therefore a need for a simpler, compact, less expensive, and easier to manufacture a surgical laser system that can be used in ophthalmology, dermatology, vascular surgery, et al., that operates at a wavelength that is effective for a variety of treatments, including photocoagulation. The present invention addresses this need, in addition to others not specified herein.

An illustrative embodiment of the present invention relates to provision of a compact, simple, ophthalmic surgical laser apparatus that enables the foregoing drawbacks to be overcome and which has additional advantages. An ophthalmic surgical laser generator utilizes a laser diode to generate a continuous low energy aiming light beam and an operating laser beam of visible light energy. Both the aiming light beam and the operating laser beam exit through a common exit lens. The exit lens can be positioned close to the operating optical system. This reduces the need for additional optical elements, as required by conventional systems with similar capabilities.

The resulting construction of the laser surgical apparatus is therefore facilitated and the production cost is reduced. Its efficiency is nevertheless improved, since the laser and light beams have a smaller number of glass-air and air-glass interfaces to cross, which are otherwise energy sinks in conventional devices prior to the present invention. The laser unit can be mounted to or integrated into ophthalmic optical equipment like a slit lamp, a surgical microscope, or a handheld lens system. Alternatively, the laser unit can be utilized for a variety of non-ophthalmic medical indications.

These and other features and advantages of the invention will become apparent from the description which follows, given by way of example, with reference to the accompanying schematic drawings.

FIGS. 1 through 7, wherein like parts are designated by like reference numerals throughout, illustrate an example embodiment of a compact surgical apparatus according to the present invention. Although the present invention will be described with reference to the example embodiment illustrated in the figures, it should be understood that many alternative forms can embody the present invention. One of ordinary skill in the art will additionally appreciate different ways to alter the parameters of the embodiment disclosed, such as the size, shape, or type of elements or materials, in a manner still in keeping with the spirit and scope of the present invention.

Turning to FIGS. 1 through 7, a compact surgical apparatus 20 embodying the invention, and corresponding method of use, are provided. The apparatus 20 includes a laser unit 1 and an operating optical system 9. The laser unit 1 includes a power regulator 3, a diode laser assembly 6 with a laser source, and a timer circuit 4. The laser unit 1 emits energy in a wavelength within the visible spectrum, such as in the violet range, nominally 405±20 nm, the blue range, nominally 445±20 nm, the green range, nominally 520±20 nm, or the red range, nominally 635±20 nm or 658±20 nm. The diode laser assembly 6 can be in the form of, for example, a diode laser or diode laser array. The figure further depicts an operator's eye 10 (e.g., the eye of the user of the apparatus) and a treated eye 11 (e.g., the eye of the patient being treated). As utilized herein, the terms laser diode and laser source are interchangeable. The laser diode assembly further includes the laser diode itself, its housing, and can further include a heat sink and means to attach it to the laser outlet.

The wavelengths of 405±20 nm, 445±20 nm, 635±20 nm, 658±20 nm, or 520±20 nm are suitable for the optics to focus and direct a treatment beam into a treatment area, an illuminator such as a slit lamp, and means for observing the treatment area.

The laser unit 1 is attachable to an operating optical system 9, such as for example, a slit lamp. This enables the laser beam and the anterior focal point of the optical system 9 to be confocal (meaning that the laser beam and the anterior focal point of the optical system 9 have the same foci).

A power source 2 provides the power to the apparatus 20. The power source 2 can be a power supply box of the operating optical system 9, e.g. slit lamp, a battery or a transformer providing the required power to drive the laser system, or other power source.

The electric current from the power source 2 passes to the laser unit 1 through the power regulator 3, which reduces the current to a lower level of between about 10-100 mA, which is sufficient to drive the laser diode at a sub-threshold level to emit a continuous broad band low energy visible light beam that is used as an aiming beam. What is meant by a 'sub-threshold level' is that the laser diode is operating below its lasing threshold. The aiming beam occurs at a laser diode baseline emission level of between about 0.1-2 mW. One of ordinary skill in the art will appreciate that a laser diode that is driven at or below its lasing threshold level produces an optical output over a wider spectrum of wavelengths, which is dominated by spontaneous emission rather than stimulated emission. For implementations of the example embodiment, the wider spectrum associated with spontaneous emission can be about 20-30 nm on both sides of the peak laser wavelength. For example, a laser diode having a peak laser wavelength of 405 nm would produce a broadband optical output of 395-425 nm when driven at or below its threshold lasing level. However, if the laser is supplied with a current that is above the threshold level, the band of the optical output would be narrow, and the spectrum would be about 405±5 nm. When operating above the lasing threshold, the output is dominated by stimulated emission. The narrow spectrum produced by a laser diode operating above the threshold level satisfies the narrow band requirement of coherent laser light, whereas the broad spectrum produced by a laser diode operating at or below the threshold level does not qualify as a laser.

One of ordinary skill in the art will appreciate that the intensity of a beam resulting from spontaneous emission will, in general, be smaller. Beams having smaller intensities are advantageous for viewing because they can present fewer risks of retinal damage or other damage of anatomical components associated with vision. The beam resulting from diode lasers operating in a sub-threshold lasing region can therefore better accommodate safety standards by decreasing health risks and greatly increasing the permissible maximum viewing exposure. Beams that are harmless and readily viewable, which can result from a diode laser operating below the lasing threshold or can result from other suitable light producing means, are herein referred to as "aiming light beams." As such, the aiming light beam of the illustrative embodiment distinguishes over normal laser beams in numerous ways, including that the character of the emitted light is such that the aiming light beam does not pose significant physical or health-related threats to operators who view the beam without eye protection.

As an additional safety feature, a laser safety filter can optionally be used to block the narrow band of the treatment laser when the laser diode is supplied by a supra-threshold current (i.e., when the laser is operating above the lasing threshold) to produce a treatment laser beam. Including a safety filter can protect the operator from excessive exposure to the laser, which could cause damage to the eye. In a similar manner, when the laser diode is supplied by a sub-threshold current (i.e., when the laser is operating below the lasing threshold), the filter will block only a narrow band around the peak wavelength of the diode, but will allow the remaining emitted wavelengths contained in the broader band of the diode beam to pass through. As shown in the bottom image of FIG. 5, fringe wavelengths that are near the upper and lower boundaries of the spectrum have smaller values of intensity. Given these smaller intensity values, passing only the fringe wavelengths can significantly diminish the normal health risks associated with viewing high-intensity beams. As such, filtering out a narrow band of high-intensity wavelengths centered around the peak laser wavelength also enables the operator to view the resulting aiming light beam with even smaller risk of eye damage due to exposure to high energy density light. This is because the resulting aiming light beam is substantially composed of lower-intensity fringe wavelengths.

The timer circuit 4 is supplied with electric current from the power source 2. When the timer circuit 4 is activated, a predetermined adjustable pulse, or train of pulses, of relatively high current is supplied to the laser diode 6 to produce a pulse, or train of pulses, of treatment laser beam. A "relatively high current" indicates that the current is above the diode laser threshold level. For example, in accordance with one embodiment of the present invention, the pulse of treatment laser beam can have a pulse duration within two sets or ranges, one in the nanosecond range (100 ns-100 microsecond) and another in a millisecond range (0.1 msec—continuous). Other ranges are possible, depending on the desired treatment. The pulse current is significantly higher than the baseline current, to provide the laser diode with enough energy to produce a pulse of laser. For example, the pulse current can be between about 500-2000 mA for treatment purposes, versus a lower baseline level of between about 10-100 mA for aiming purposes. The characteristic of the laser pulse(s) may depend on the pre-determined settings, as would be understood by those of ordinary skill in the art. One of ordinary skill in the art will additionally appreciate that it is the pulse current being significantly higher than the baseline current that is relevant to the present invention. The specific current levels are merely illustrative of an example implementation. The timer circuit 4 is activated by triggering a laser switch 5, such as a hand or foot switch trigger.

At the conclusion of the laser pulse(s), the laser diode emission level returns back to the baseline as the aiming beam supplied by the power regulator 3. The laser beam emitted from the diode laser assembly 6 passes through a laser outlet assembly 7, which directs and controls the size and focus of the laser beam. The laser outlet assembly 7 has a number of rheostats or switches to control the intensity and duration of the laser treatment beam pulse(s). The laser outlet assembly 7 includes one or more lenses, apertures, and/or prisms through which the laser energy passes.

Figure 4:
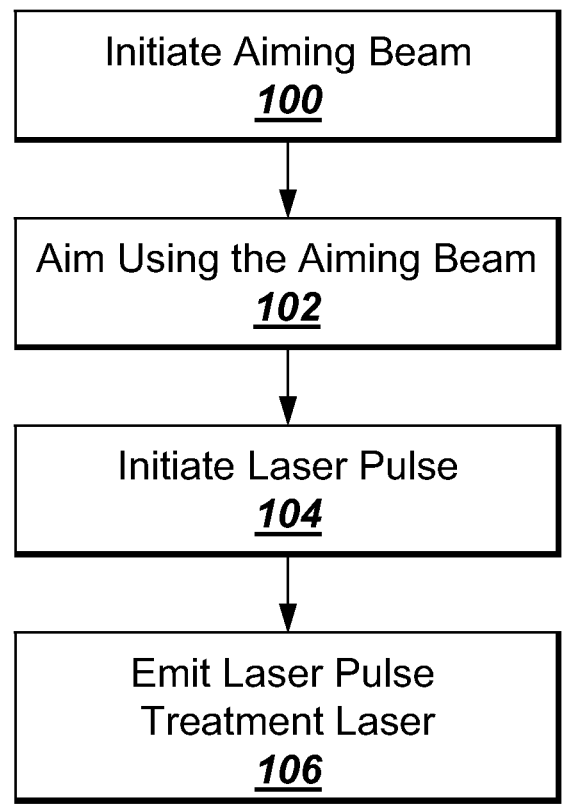
FIG. 4 is a flowchart illustrating one example method of implementation of the compact surgical apparatus according to one embodiment of the present invention.

Turning now to FIG. 4, a brief description of the method of utilizing the compact surgical apparatus according to the present invention is illustrated. The method of use begins (after any initial setup steps) with the provision of power to the diode laser assembly 6 of the laser unit 1 through the power regulator 3 to initiate an aiming beam (step 100). The current is provided at a level sufficient to drive the laser diode to emit a continuous low energy visible laser beam that is used as the aiming beam. The user utilizes the aiming beam to locate a desired area for treatment on the treated eye 11, making any necessary adjustments to the laser beam at the laser outlet assembly 7 (step 102).

When a treatment laser beam is desired, the user activates the timer circuit 4 using the laser switch 5 (step 104). The timer is then supplied with electric current from the power source 2. When the timer circuit 4 is activated, a predetermined adjustable pulse, or train of pulses, of relatively higher current is supplied to the laser diode 6 and laser pulses emit in the direction of the treated eye 11, producing a treatment laser beam (step 106).

The various conventional components described herein and their construction individually are well known to those skilled in the art and therefore will not be described in greater detail herein.

Figure 5:
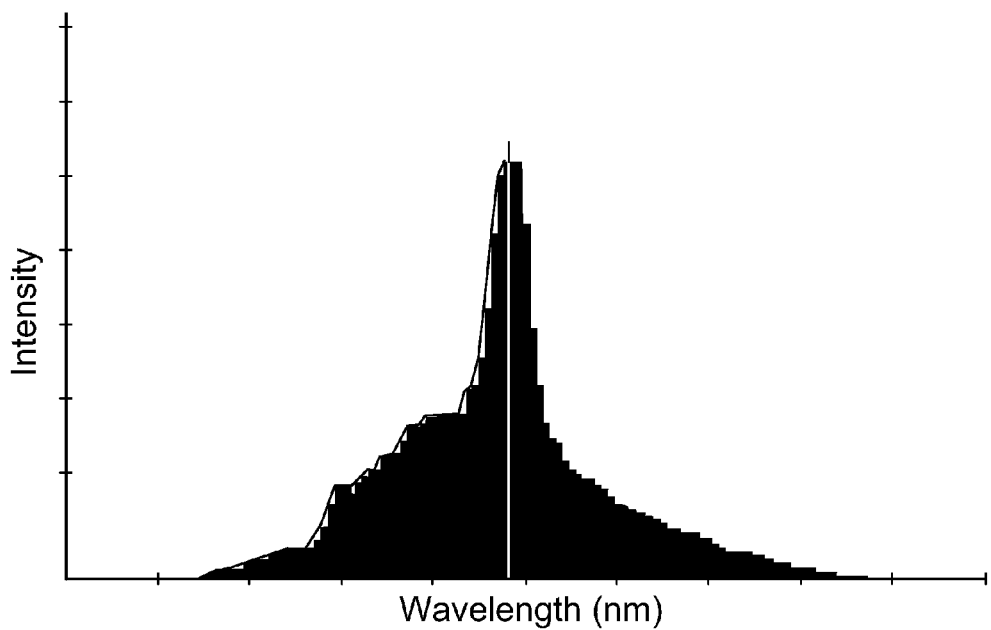
FIG. 5 is a chart illustrating spectrographic analysis of a typical laser diode, in accordance with aspects of the present invention.
Figure 5:
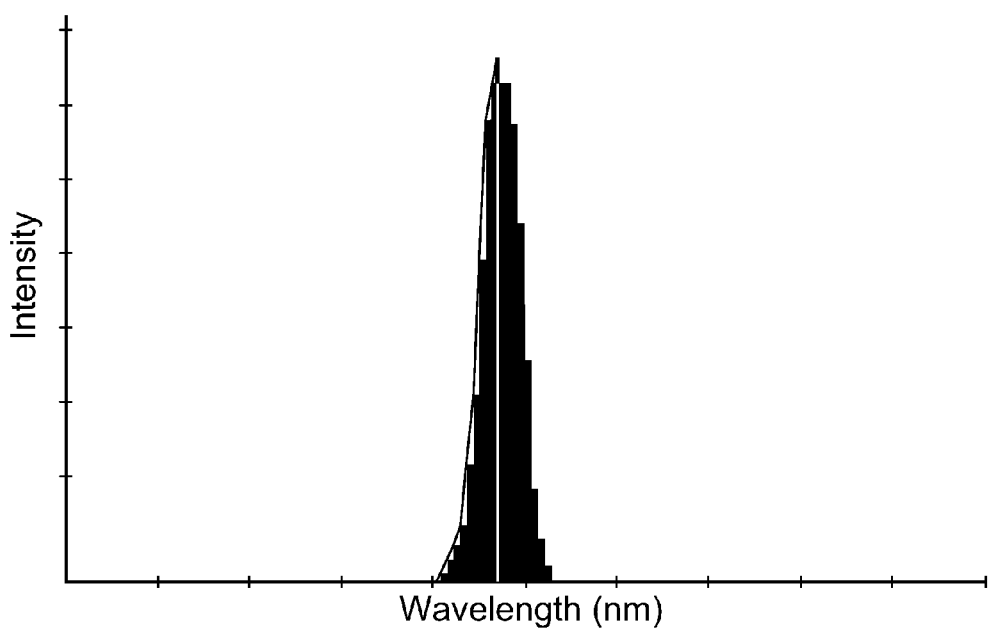

FIG. 5 illustrates comparative spectrographic analyses of two laser diodes. The top image of FIG. 5 shows the optical output of a laser diode that is driven by a current at or below the threshold level (i.e., sub-threshold current). The optical output is produced by spontaneous emission, and the band is too broad to satisfy the narrow band requirement of a coherent laser. The bottom portion of FIG. 5 shows the optical output of a laser diode that is driven by a current above the threshold level (i.e., supra-threshold current). The optical output is produced by stimulated emission of radiation. Unlike the top image, the band depicted in the bottom image is sufficiently narrow to qualify as the band of a coherent laser.

A diode laser assembly operating at a wavelength in the visible spectrum, especially in the range of 405±20 nm, 445±20 nm, 635±20 nm, 658±20 nm, or 520±20 nm, is very well absorbed by the suture material most commonly used during ophthalmic surgeries, e.g., nylon threads or sutures. Laser energy operating at the aforementioned wavelength range, and a power level of generally less than 500 mWatts, can be used to cut stitches buried in the ocular tissues like the cornea or under the skin of the eye conjunctiva following glaucoma surgery.

The compact surgical apparatus in accordance with the present invention is able to provide laser emissions with similar properties to those in the prior art designed to effect photocoagulation. However, in contrast to the dual laser systems of the prior art (separate lasers for aiming and treatment), the compact surgical apparatus in accordance with the present invention has the ability to exhibit these desired laser emission properties with a single wavelength range from a single laser source. Consequentially, the compact surgical apparatus of the present invention provides a single, simple, economical, and compact apparatus. It can perform a number of different photocoagulation procedures. The apparatus of the present invention enables a medical professional to use a single, compact device to treat a number of disorders involving the eye. The compactness of the apparatus also enables the apparatus to be portable.

The present invention is useful for a number of ophthalmic indications that previously would have required different wavelengths, and thus numerous laser devices, or more complex multi-laser devices. It is especially effective for those procedures that have previously utilized Krypton, Argon, or infrared 810 nm diode lasers. Many ophthalmic diseases and treatment modalities can be treated using the apparatus of the present invention.

Mal-directed eye lashes are a common condition resulting from eyelid scarring secondary to infection, burns, or medications. The mal-directed lashes rub against the eye surface leading to inflammation and scarring of the ocular surface. This condition can be treated using laser photocoagulation, which coagulates the eyelash follicle and prevents re-growth of rubbing lashes.

Glaucoma refers to a group of conditions resulting in optic nerve damage, which diminishes sight. Abnormally high pressure inside the eye is often the cause of the damage. Glaucoma treatment can require creation of a hole in the colored part of the eye, i.e., the iris, utilizing a laser in a procedure called laser peripheral iridotomy. Prior to the present invention, either Argon or Nd-YAG lasers have been utilized for such a procedure. The surgical laser device of the present invention combines the advantages of Argon laser (less likelihood of bleeding, works in patients with thick iris) and the Nd-Yag Laser (very short pulse/pulses and a very focused beam). The surgical laser device of the present invention can also be used in a procedure known as laser trabeculoplasty, where the laser is used to improve the function of the drain of the eye as relating to the trabecular meshwork to relieve the eye pressure. The present invention provides a more compact and easy to use apparatus for conducting such a procedure. During the glaucoma filtering surgery, nylon stitches are used to control the flow in the surgery site. Those stitches are deep under the skin of the eye and they require a laser to cut them in the post-operative period to achieve better eye pressure control. This procedure is referred to as selective laser suturelysis, and is conventionally done by an Argon laser. The present invention can perform the same procedure, in part due to its ability to target 10-0 nylon, as described below.

Diabetic retinopathy is characterized by retinal dot and blot hemorrhages, micro-aneurysms and exudates in early stages. Proliferative diabetic retinopathy, a late stage of the disease, is characterized by neovascularization and vitreous or pre-retinal hemorrhages. Photocoagulative treatments can successfully treat these problems. In particular, pan-retinal photocoagulation is effective for causing regression of neovascular tissues.

In addition, the compact surgical apparatus of the present invention can also be utilized as a photocoagulator for treating retinal vein occlusion, rhegmatogenous peripheral retinal lesions, and retinal breaks and for prophylactic peripheral retinopexy prior to silicone oil removal.

Additional benefits of the present invention, apart from its evident versatility, include high efficiency and thus lower power requirements, and longer life due to reduced need for maintenance. Specifically, the efficiency achieved by the compact surgical apparatus is improved relative to conventional devices because there is less manipulation of the laser energy with the present device than with conventional devices. Because there is only one laser, instead of two, the number of components required for the compact surgical apparatus system is less than prior conventional devices, and therefore, the maintenance requirements are diminished relative to conventional devices as well.

The present invention includes new diode laser designs providing high beam quality that can directly be focused using lenses to produce a small spot size of about 50 microns verses typical spot sizes of up to 400 microns. The ability to generate a beam with a spot size of about 50 microns provides the compact surgical apparatus with the ability to be utilized in treatments requiring 100 microns or less spot size. Examples of treatments include selective laser suturelysis, and minimally destructive procedures, such as ablating maldirected lashes. A spot size of about 100 micros or less is preferred in such applications.

In a preferred embodiment, the laser power delivered and the pulse duration of the laser are determined by the laser driving circuits, which provide precise digital control of the laser parameters without the need to use cumbersome complex optical elements. Other embodiments may include adaptors to indirect opthalmoscopes, or may include a slit lamp that has already included in its structure the spot size selection mechanism as described above.

In accordance with alternate embodiments of the present invention, the specific laser parameters can differ, depending on the particular application of the laser device. For example, as previously described, the diode laser assembly operating in the range of 405±20 nm, 445±20 nm, 635±20 nm, 658±20 nm, or 520±20 nm is absorbed by suture material used during ophthalmic surgeries, e.g., nylon threads or sutures. At these wavelengths, and at a power level of less than 500 mW, laser energy can be used to cut stitches buried in the ocular tissues like the cornea or under the skin of the eye (conjunctiva) following glaucoma surgery.

In addition to the 405±20 nm, 445±20 nm, 635±20 nm, 658±20 nm, or 520±20 nm wavelengths, other wavelength laser diodes may additionally benefit from the single laser diode configuration of the present invention. For example, violet-blue lasers having wavelengths of about 400-488 nm (±20 nm), or green lasers having wavelengths of about 520-555 nm (±20 nm) can also be configured to have a single laser diode operable to emit an aiming beam and a treatment beam from the same laser diode. Violet-blue and green wavelength lasers are useful for the same applications as red lasers. Any wavelength in the visible spectrum, but particularly blue and green wavelengths, emitting short duration pulses in the nanosecond to microsecond range, can be used to treat the retinal pigment epithelium (RPE). As such, these wavelengths may be useful to treat diseases of the retina or macula, such as macular degeneration, or to stimulate the RPE for drug delivery through the RPE. Violet-blue and green wavelengths can also be used at longer pulse durations (microsecond to millisecond) to perform conventional photocoagulation of ocular tissues.

In terms of the configuration, the compact surgical apparatus 20 of the present invention is the same for the violet-blue and green lasers as the configuration for the red laser described herein, other than the provision of a different wavelength laser diode (thus producing the different color/wavelength laser emissions). As such, further detail of the compact surgical apparatus 20 with green or violet-blue laser is not necessary.

Figure 6:
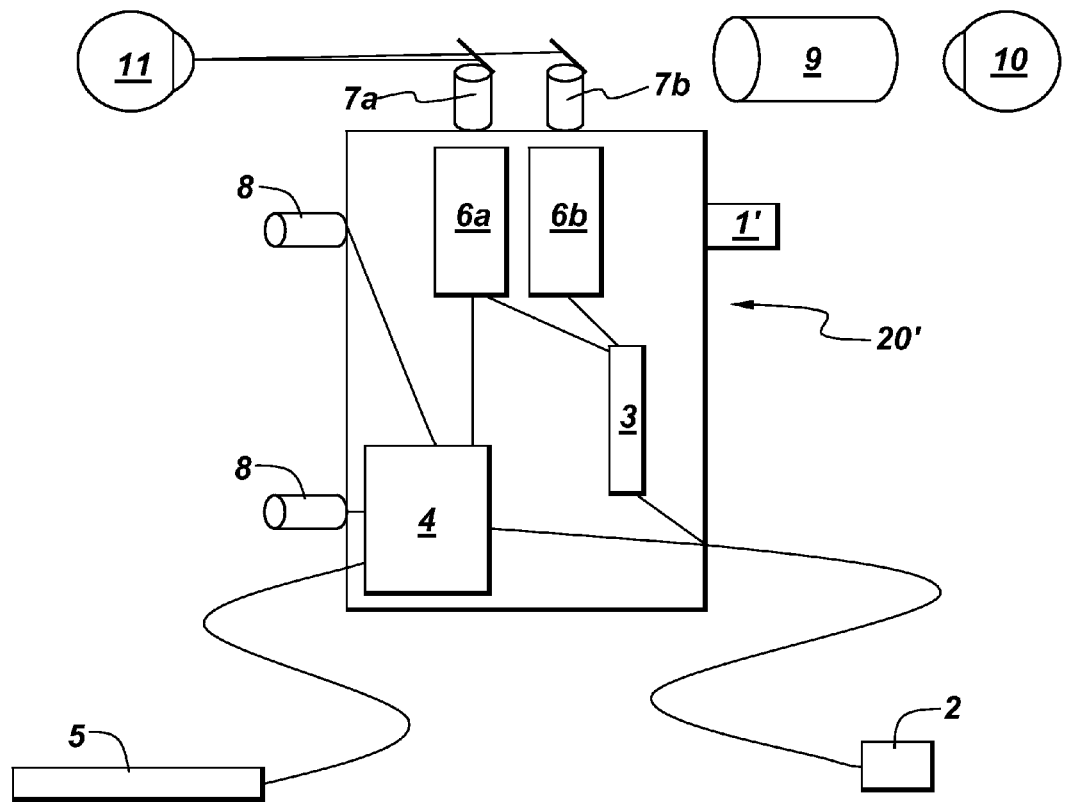
FIG. 6 is a schematic illustration of a compact surgical apparatus according to one embodiment of the present invention.

In accordance with yet another embodiment of the present invention, more than one laser diode of the same or different wavelengths can be used for the compact surgical apparatus. FIG. 6 shows a compact surgical apparatus 20' embodying the invention. The apparatus 20' includes a laser unit 1' and the operating optical system 9. The laser unit 1' includes a power regulator 3, two diode laser assemblies 6a, 6b, and a timer circuit 4. The laser unit 1' emits energy in a wavelength within the visible spectrum, such as in the red or blue, green ranges. The diode laser assemblies 6a, 6b can be in the form of, for example, a diode laser or diode laser array.

The laser unit 1' is attachable to the operating optical system 9, such as for example, a slit lamp. This enables the laser beam and the anterior focal point of the optical system 9 to be confocal (meaning that the laser beam and the anterior focal point of the optical system 9 have the same foci). The power source 2 provides the power to the apparatus 20'. The power source 2 can be a power supply box of the operating optical system 9, e.g. slit lamp, a battery or a transformer providing the required power to drive the laser system, or other power source.

The electric current from the power source 2 passes to the laser unit 1' through the power regulator 3, which reduces the current to a lower level of between about 10-100 mA, which is sufficient to drive the laser diode assemblies 6a, 6b to emit a continuous low energy visible laser beam that is used as an aiming beam. There may be separate power regulators 3, one for each laser diode assembly 6a, 6b, or a single power regulator 3 used by one laser diode assembly 6a, 6b at a time.

The timer circuit 4 is supplied with electric current from the power source 2. When the timer circuit 4 is activated, a pre-determined adjustable pulse, or train of pulses, of relatively high current is supplied to the laser diode assembly 6a or 6b to produce a pulse of treatment laser beam. The characteristic of the laser pulse, or train of pulses, may depend on the pre-determined pulse settings, as would be understood by those of ordinary skill in the art. As noted above, a separate timer circuit 4 may be used for each laser diode assembly 6a, 6b, or the same circuit may be used on one laser diode assembly 6a, 6b at a time.

At the conclusion of the laser pulse, the laser diode emission level returns back to the baseline as the aiming beam supplied by the power regulator 3. The laser beam emitted from the diode laser assemblies 6a, 6b passes through the laser outlet assemblies 7a, 7b, in order, which direct and control the size and focus of the laser beams. The laser unit 20' has a number of rheostats or switches to control the intensity and duration of the laser treatment beam pulse. Each laser outlet assembly 7a, 7b includes a lens/lens assembly through which the laser energy passes, and a highly reflective mirror to direct the laser beam.

To be clear, this configuration of compact surgical apparatus 20' differs from the conventional ophthalmic laser systems in that each laser diode assembly 6a, 6b is capable of emitting both the aiming light beam and the treatment laser beam. The reason for different and separate assemblies 6a, 6b is to provide added capabilities relating to the wavelength and other laser characteristics while still having a single apparatus 20'. This is not the same as conventional systems having a separate laser or light source for aiming and a separate laser source for treatment. One of ordinary skill in the art will additionally appreciate that the above description of two laser diode assemblies is merely representative of the concept of having a plurality of laser diode assemblies. As such, the present invention is not intended to be limited to one, or two, laser diode assemblies, but can include more. Each laser diode assembly, however, is intended to operate as described herein, where a single laser diode assembly has two power settings, such that both aiming and treatment beams can be emitted from the same laser diode source.

Figure 7:
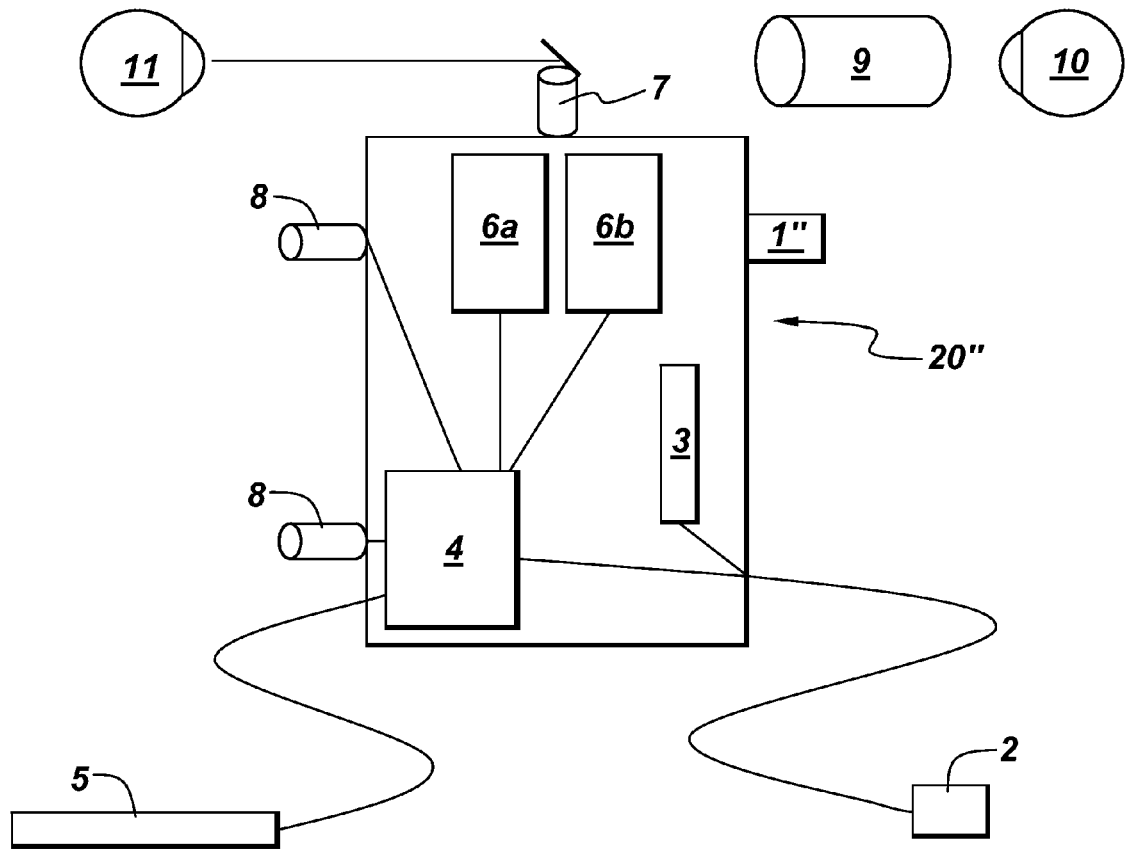
FIG. 7 is a schematic illustration of a compact surgical apparatus according to one embodiment of the present invention.

In accordance with yet another embodiment of the present invention, more than one laser diode of the same or different wavelengths can be used as the laser source for the compact surgical apparatus. FIG. 7 shows a compact surgical apparatus 20" embodying the invention. The apparatus 20" includes a laser unit 1" and the operating optical system 9. The laser unit 1" includes a power regulator 3, two diode laser assemblies 6a, 6b, and a timer circuit 4. The laser unit 1" emits energy in a wavelength within the visible spectrum, such as in the red or violet-blue, or green ranges. The diode laser assemblies 6a, 6b can be in the form of, for example, a diode laser, or diode laser array.

The laser unit 1" is attachable to the operating optical system 9, such as for example, a slit lamp. This enables the laser beam and the anterior focal point of the optical system 9 to be confocal (meaning that the laser beam and the anterior focal point of the optical system 9 have the same foci). The power source 2 provides the power to the apparatus 20". The power source 2 can be a power supply box of the operating optical system 9, e.g. slit lamp, a battery or a transformer providing the required power to drive the laser system, or other power source.

The electric current from the power source 2 passes to the laser unit 1" through the power regulator 3, which reduces the current to a lower level of between about 10-100 mA, which is sufficient to drive the laser diode assemblies 6a, 6b to emit a continuous low energy visible laser beam that is used as an aiming beam. There may be separate power regulators 3, one for each laser diode assembly 6a, 6b, or a single power regulator 3 used by one laser diode assembly 6a, 6b at a time.

The timer circuit 4 is supplied with electric current from the power source 2. When the timer circuit 4 is activated, a pre-determined adjustable pulse, or train of pulses, of relatively high current is supplied to the laser diode assembly 6a or 6b to produce a pulse of treatment laser beam. The characteristic of the laser pulse(s) may depend on the pre-determined pulse settings, as would be understood by those of ordinary skill in the art. As noted above, a separate timer circuit 4 may be used for each laser diode assembly 6a, 6b, or the same circuit may be used on one laser diode assembly 6a, 6b at a time.

At the conclusion of the laser pulse(s), the laser diode emission level returns back to the baseline as the aiming beam supplied by the power regulator 3. The laser beam emitted from the diode laser assemblies 6a, 6b passes through the laser outlet assembly 7, which direct and control the size and focus of the laser beams. The laser unit 20" has a number of rheostats or switches to control the intensity and duration of the laser treatment beam pulse. The laser outlet assembly 7 includes a lens/lens assembly through which the laser energy passes, and a highly reflective mirror to direct the laser beam.

To be clear, this configuration of compact surgical apparatus 20" differs from the conventional ophthalmic laser systems in that each laser diode assembly 6a, 6b is capable of emitting both the aiming light beam and the treatment laser beam. The reason for different and separate assemblies 6a, 6b is to provide added capabilities relating to the wavelength and other laser characteristics while still having a single apparatus 20". This is not the same as conventional systems having a separate laser source for aiming and a separate laser source for treatment. One of ordinary skill in the art will additionally appreciate that the above description of two laser diode assemblies is merely representative of the concept of having a plurality of laser diode assemblies. As such, the present invention is not intended to be limited to one, or two, laser diode assemblies, but can include more. Each laser diode assembly, however, is intended to operate as described herein, where a single laser diode assembly has two power settings, such that both aiming and treatment beams can be emitted from the same source.

Accordingly, a compact laser device and method for ophthalmic procedures is described herein. The laser device and method can be used in ophthalmic surgeries, e.g. cutting deep stitches in the context of surgical management of ophthalmic disorders, e.g. Glaucoma or corneal grafts. The device is a compact, portable surgical apparatus, including a generator of a laser in the visible spectrum for emitting both an aiming (marker) light beam of relatively low power, and an operating treatment laser beam of relatively high power from at least one laser diode and passing through the same optical elements without using a fiber-optic delivery system. The laser diode can provide continuous or pulsed operating laser without utilizing a mechanical shutter.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A compact surgical apparatus, comprising:
   a laser unit, comprising:
      a power regulator;
      a diode laser assembly having a single diode laser source;
      a laser trigger mechanism; and
   a laser outlet assembly;
   wherein the laser unit emits an aiming light beam and a treatment laser beam both from the single diode laser through the laser outlet assembly, the aiming light beam having a first energy level and the treatment laser beam having a second energy level that is substantially greater than the first energy level of the aiming light beam;
   wherein the laser unit has a lasing threshold, and further wherein the first energy level is below the lasing threshold and the second energy level is above the lasing threshold.

2. The compact surgical apparatus of claim 1, wherein the laser unit emits energy in a wavelength within the visible spectrum.

3. The compact surgical apparatus of claim 1, wherein the laser unit emits energy at a wavelength selected from the group consisting of about 405±20 nm, about 445±20 nm, about 635±20 nm, about 658±20 nm, and about 520±20 nm.

4. The compact surgical apparatus of claim 1, wherein the power regulator is configured to supply the diode laser assembly with a current of about 10-100 mA or about 500-2,000 mA.

5. The compact surgical apparatus of claim 1, wherein the aiming light beam and the treatment laser beam each have a spot size of about 50 microns.

6. The compact surgical apparatus of claim 1, further comprising a timer circuit for activating one or more predetermined, adjustable pulses, wherein the laser outlet assembly includes a lens assembly comprising one or more lenses configured in such a way as to direct the paths of the aiming light beam and the treatment laser beam.

7. A system for surgical procedures, comprising:
a compact surgical apparatus, comprising:
a laser unit, comprising:
a power regulator;
a diode laser assembly having a single diode laser source;
a laser trigger mechanism; and
a laser outlet assembly;
wherein the laser unit emits an aiming light beam and a treatment laser beam both from the single diode laser through the laser outlet assembly, the aiming light beam having a first energy level and the treatment laser beam having a second energy level that is substantially greater than the first energy level of the aiming light beam; and
an operating optical system coupled with the compact surgical apparatus;
wherein the laser unit has a lasing threshold, and further wherein the first energy level is below the lasing threshold and the second energy level is above the lasing threshold.

8. The system of claim 7, wherein the laser unit emits energy in a wavelength within the visible spectrum.

9. The system of claim 7, wherein the laser unit emits energy at a wavelength selected from the group consisting of about 405±20 nm, about 445±20 nm, about 635±20 nm, about 658±20 nm, and about 520±20 nm.

10. The system of claim 7, wherein the power regulator is configured to supply the diode laser assembly with a current of about 10-100 mA or about 500-2,000 mA.

11. The system of claim 7, wherein the aiming light beam and the treatment laser beam each have a spot size of about 50 microns.

12. The system of claim 7, further comprising a timer circuit for activating one or more predetermined, adjustable pulses, wherein the laser outlet assembly includes a lens assembly comprising one or more lenses for directing the paths of the aiming light beam and the treatment laser beam.

13. A method of using a compact surgical apparatus, comprising:
providing power to a diode laser assembly of a laser unit having a single diode laser source through a power regulator;
controlling a power level of the laser unit using the power regulator to emit an aiming light beam from the single diode laser at a first power level;
activating a trigger to initiate a treatment laser pulse from the single diode laser of the laser unit having a second power level substantially greater in magnitude than the first power level of the aiming light beam; and
emitting the treatment laser pulse to a targeted treatment area;
wherein the laser unit has a lasing threshold, and further wherein the first energy level is below the lasing threshold and the second energy level is above the lasing threshold.

14. The method of claim 13, wherein the laser unit emits energy in a wavelength within the visible spectrum.

15. The method of claim 13, wherein the laser unit emits energy at a wavelength selected from the group consisting of about 405±20 nm, about 445±20 nm, about 635±20 nm, about 658±20 nm, and about 520±20 nm.

16. The method of claim 13, wherein using the power regulator comprises using the power regulator to supply the diode laser assembly with a current of about 10-100 mA, and further wherein activating a trigger comprises activating a trigger to supply a current of about 500-2,000 mA from the power regulator to the laser diode assembly.

17. The method of claim 13, wherein the aiming light beam and the treatment laser beam each have a spot size of about 50 microns.

18. The method of claim 13, further comprising the steps:
directing the paths of the aiming light beam and the treatment laser beam with a lens assembly comprising one or more lenses; and
emitting one or more subsequent predetermined, adjustable treatment laser pulses using a timer circuit.

19. A compact surgical apparatus, comprising:
a laser unit, comprising:
a power regulator;
a first diode laser assembly having a single diode laser source;
a second diode laser assembly having a single diode laser source;
a laser trigger mechanism; and
a laser outlet assembly;
wherein the laser unit emits an aiming light beam and a treatment laser beam both from of the first diode laser assembly and the second diode laser assembly through the laser outlet assembly, the aiming light beam having a first energy level and the treatment laser beam having a second energy level that is substantially greater than the first energy level of the aiming light beam;
wherein the laser unit has a lasing threshold, and further wherein the first energy level is below the lasing threshold and the second energy level is above the lasing threshold.

20. The compact surgical apparatus of claim 19, wherein the laser unit emits energy in a wavelength within the visible spectrum.

21. The compact surgical apparatus of claim 19, wherein the laser unit emits energy at a wavelength selected from the group consisting of about 405±20 nm, about 445±20 nm, about 635±20 nm, about 658±20 nm, and about 520±20 nm.

22. The compact surgical apparatus of claim 19, wherein the power regulator is configured to supply the first diode laser assembly with a current of about 10-100 mA and the second diode laser assembly with a current of about 500-2,000 mA.

23. The compact surgical apparatus of claim 19, wherein the aiming light beam and the treatment laser beam each have a spot size of about 50 microns.

24. The compact surgical apparatus of claim 19, further comprising a timer circuit for activating one or more predetermined, adjustable pulses, wherein the laser outlet assembly includes a lens assembly comprising one or more lenses configured in such a way as to direct the paths of the aiming light beam and the treatment laser beam.

25. A compact surgical apparatus, comprising:
a laser unit, comprising:
a power regulator;
a first diode laser assembly having a single diode laser source;
a second diode laser assembly having a single diode laser source;
a laser trigger mechanism;
a first laser outlet assembly; and
a second laser outlet assembly;

wherein the laser unit emits an aiming light beam and a treatment laser beam both from both of the first diode laser assembly and the second diode laser assembly through the first and second laser outlet assembly, the aiming light beam having a first energy level and the treatment laser beam having a second energy level that is substantially greater than the first energy level of the aiming light beam;

wherein the laser unit has a lasing threshold, and further wherein the first energy level is below the lasing threshold and the second energy level is above the lasing threshold.

26. The compact surgical apparatus of claim 25, wherein the laser unit emits energy in a wavelength within the visible spectrum.

27. The compact surgical apparatus of claim 25, wherein the laser unit emits energy at a wavelength selected from the group consisting of about 405±20 nm, about 445±20 nm, about 635±20 nm, about 658±20 nm, and about 520±20 nm.

28. The compact surgical apparatus of claim 25, wherein the power regulator is configured to supply the first diode laser assembly with a current of about 10-100 mA and the second diode laser assembly with a current of about 500-2,000 mA.

29. The compact surgical apparatus of claim 25, wherein the aiming light beam and the treatment laser beam each have a spot size of about 50 microns.

30. The compact surgical apparatus of claim 25, further comprising:

a timer circuit for activating one or more predetermined, adjustable pulses; and one or more lens assemblies, each of the one or more lens assemblies comprising one or more lenses configured in such a way as to direct the paths of the aiming light beam and the treatment laser beam.

* * * * *